(12) United States Patent
Boussignac

(10) Patent No.: US 8,887,728 B2
(45) Date of Patent: Nov. 18, 2014

(54) RESPIRATORY ASSISTANCE MASK

(76) Inventor: Georges Boussignac, Antony (FR)

( * ) Notice: Subject to any disclaimer, the term of this patent is extended or adjusted under 35 U.S.C. 154(b) by 344 days.

(21) Appl. No.: 13/535,631

(22) Filed: Jun. 28, 2012

(65) Prior Publication Data
US 2013/0008445 A1   Jan. 10, 2013

(30) Foreign Application Priority Data

Jul. 5, 2011   (FR) ...................................... 11 02101

(51) Int. Cl.
*A61M 11/00*   (2006.01)
*A61M 16/06*   (2006.01)

(52) U.S. Cl.
CPC ........... *A61M 16/06* (2013.01); *A61M 16/0616* (2013.01); *A61M 16/0622* (2013.01)
USPC ............. 128/206.24; 128/207.11; 128/201.24

(58) Field of Classification Search
USPC ............. 128/205.25, 201.22, 201.23, 201.24, 128/201.29, 206.21, 206.24, 206.26, 128/206.28, 207.11, 207.13
See application file for complete search history.

(56) References Cited

U.S. PATENT DOCUMENTS

| | | | |
|---|---|---|---|
| 3,330,273 A | 7/1967 | Bennett | |
| 6,467,482 B1 * | 10/2002 | Boussignac | 128/206.24 |
| 6,871,649 B2 * | 3/2005 | Kwok et al. | 128/206.24 |
| 7,278,428 B2 * | 10/2007 | Fini et al. | 128/206.26 |
| 7,523,754 B2 * | 4/2009 | Lithgow et al. | 128/206.24 |
| 7,950,392 B2 * | 5/2011 | Kwok et al. | 128/206.24 |
| 8,573,214 B2 * | 11/2013 | Davidson et al. | 128/206.24 |
| 2003/0019495 A1 * | 1/2003 | Palkon et al. | 128/206.21 |

FOREIGN PATENT DOCUMENTS

WO    WO 2006/074513 A1    7/2006

OTHER PUBLICATIONS

French Preliminary Search Report completed Feb. 8, 2012 from corresponding French Application No. 11/02101 filed Jul. 5, 2011 (2 pages).

* cited by examiner

*Primary Examiner* — Steven Douglas
(74) *Attorney, Agent, or Firm* — Klein, O'Neill & Singh, LLP

(57) ABSTRACT

According to the present device, system, and method, the respiratory assistance mask comprising a hollow body bounding an internal chamber provided with a respiratory gas inlet and outlet, and a bearing member is remarkable in that it also comprises: a flexible membrane inserted on said bearing member and being able to be interposed between said bearing member and the face of said patient; and a multi-perforated internal skirt inserted, thru one of its two contours, on said bearing member and surrounded, at least partially, by said flexible membrane, the free contour of said skirt extending in direction of said internal chamber.

8 Claims, 2 Drawing Sheets

RESPIRATORY ASSISTANCE MASK

CROSS-REFERENCE TO RELATED APPLICATION

This regular utility application claims priority to French Application No. 11/02101, filed Jul. 5, 2011, the contents of which are expressly incorporated herein by reference.

FIELD OF ART

The present device, system, and method are related to a nasal or bucconasal respiratory assistance mask being usable particularly on patients, the spontaneous respiration of which is absent or insufficient.

BACKGROUND

Respiratory assistance masks are already known, to be able to bring in the lungs of a patient respiratory gas from an external source, said respiratory masks comprising:

a hollow body, the internal volume defines a chamber provided with a respiratory gas inlet formed with a tip being integral with the body bottom able to be connected with said source, the hollow body being adapted to be applied against the patient's face while enclosing the nose and/or the mouth of the latter;

an opening forming the respiratory gas outlet and adapted to be connected with patient's respiratory tract; and a flexible bearing member—for example under the shape of an inflatable bead or a closed pore foam bead—bordering the contour of said opening and adapted to abut against patient's face so as to provide sealing between said respiratory gas outlet and the outside.

Furthermore, it is known that the flexibility of the bearing member confers to the hollow body a certain freedom of orientation once the mask being positioned on the patient's face. In other words, the bearing member provides an orientation function in the hollow body space, thereby allowing for a manipulation of the latter with no discomfort for the patient.

However, despite its flexibility, such a bearing member cannot perfectly meet some irregularities of patient's face, on which it is applied so that:

leaks locally occur, leading to expensive losses of respiratory gas; and there is a risk that respiratory gas, passing between the bearing member and the face further to sealing defects, enters patient's eyes, generating ocular irritations and conjunctivities.

To alleviate such sealing defects, the application force of the mask on the face is generally increased—for example thru elastic straps passing behind patient's head—so as to be able to press the bearing member against the face.

However, despite the fact that it favors the appearance of scabs, the thorough application of the respiratory mask on patient's face leads to a large pressure of the flexible bearing member, thereby tending to make it more rigid. Due to the loss of the flexibility thereof, the bearing member only provides a limited orientation of the hollow body relative to the face.

SUMMARY

A uniform sealing is preferred between the bearing member and the face and the mask must be applied with force on the face, thereby reducing the amplitude of the movement of the hollow body with respect to the face.

An object of the present device, system, and method is to remedy such disadvantages and particularly to allow for some orientation amplitude of the hollow body relative to patient's face—when the mask is in position—while providing a uniform sealing between the mask and the face.

To this end, according to the present device, system, and method, the respiratory assistance mask allowing to bring, in the lungs of a patient, respiratory gas from an external source, said mask comprising:

a hollow body, the internal volume of which defines an internal chamber provided with a respiratory gas inlet adapted to be connected to said source;

an opening forming the respiratory gas outlet and which is adapted to be connected to a respiratory tract of said patient; and a flexible bearing member bordering the contour of said opening and which is adapted to be interposed between the face of said patient and said hollow body, is remarkable in that it further comprises:

a flexible membrane inserted on said bearing member and being able to be interposed between said bearing member and the face of said patient; and a multi-perforated internal skirt inserted, thru one of the two contours thereof, on said bearing member and surrounded, at least partially, by said flexible membrane, the free contour of said skirt extending in the direction of said internal chamber, so that respiratory gas is adapted to cross the perforations of said skirt, from said inlet, so as to stretch said membrane and apply it tightly against patient's face.

Thus, thanks to the present device, system, and method, respiratory gas may cross the perforations of the skirt so as to stretch the flexible membrane and press it against patient's face while adapting to the morphology thereof. That provides a uniform sealing between the face and the mask, along the opening of the internal chamber. Because a convenient sealing is obtained by application of the membrane, the application force of the respiratory mask on the patient face may substantially be reduced, thus cancelling the risk of scabs appearing upon an extended wearing of the mask while reducing the use discomfort for the patient. The mask application force being reduced, the bearing member is not or only a little pressed so that it maintains its whole flexibility and fully provides its orientation function for the hollow body with respect to the face, once the mask being in position. Thus, thanks to the present device, system, and method, the orientation function of the hollow body is implemented by the bearing member, while the uniform sealing between the mask and the face is mainly obtained by the flexible membrane. No compromise is now necessary between the orientation of the hollow body and the sealing of the mask on the face.

Advantageously, to improve the sealing performed by the flexible membrane by providing a uniform distribution for the respiratory gas, said perforations are regularly distributed along the circumference of said skirt. Of course, alternatively, any other desired distribution of the perforations could be envisaged.

Preferably, said perforations are arranged in said skirt opposite said membrane to provide a perfect application of the membrane against the face and avoid leak formation.

Moreover, each of said perforations can be present under the shape of an oblique hole arranged in said skirt so as to orient the respiratory gas toward said membrane, while limiting turbulences at the hole inlets.

Further, the free end of said membrane preferably extends toward the inside of said opening, thereby allowing to easily adapt the mask on various different types of face.

Said bearing member can be present under the shape of an inflatable bead or a closed pore foam bead. It goes without saying that it could equally take the form of a bellows or possibly any other convenient shape.

Advantageously, said flexible or semi-rigid skirt is shaped to the form of the face so as to make the adaptation and the maintenance of the mask on the latter easier.

Moreover, said flexible membrane can be made in a plastic film of a thickness of a few microns.

BRIEF DESCRIPTION OF THE DRAWINGS

The figures of the accompanying drawing will make well understood how the present device, system, and method can be implemented. On such FIGS., identical references denote similar elements.

DETAILED DESCRIPTION

Figure 1:
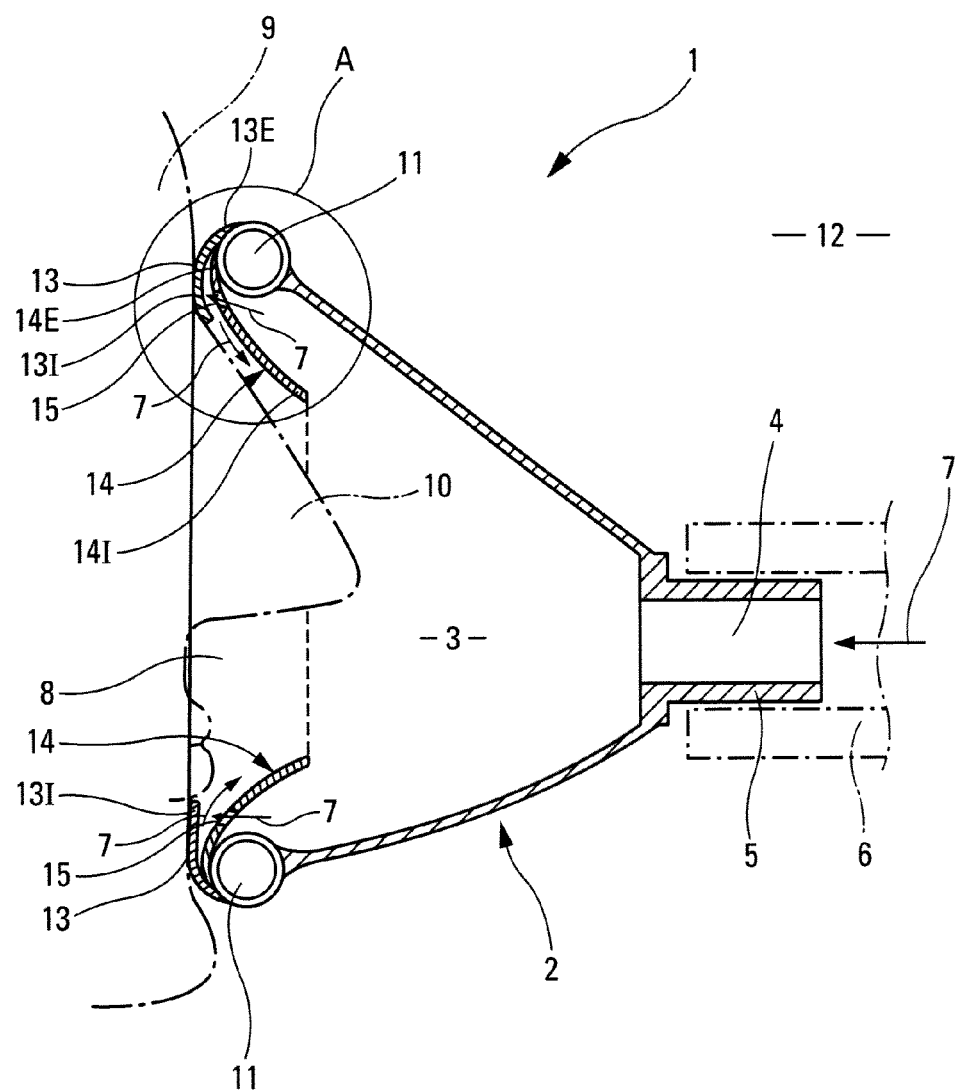
FIG. 1 schematically represents according to an axial section an exemplary embodiment of a respiratory assistance mask according to the present device, system, and method.

The respiratory assistance mask 1 according to the present device, system, and method shown in the figures, comprises a hollow shell 2 bounding an internal chamber 3. At the bottom of the shell 2, a respiratory gas inlet 4 is arranged, for example, thanks to a tubular tip 5, being integral with said shell 2, which could be connected to a respiratory gas source (not shown) for example a pressure cylinder, thru an appropriate pipe 6. On FIG. 1, the arrival of fresh respiratory gas is symbolized by the arrow 7.

The internal chamber 3 comprises a respiratory gas outlet made by the opening 8 in said shell 2. The latter is adapted to be applied, thru the opening 8 thereof, on the face 9 of a patient (represented in mixed lines), thus enclosing the nose 10 of the latter.

The respiratory mask 1 further comprises a bearing member under the shape of an inflatable bead 11 with a thin wall, being integral with the shell 2 and following the contour of the opening 8 of the latter. The bead 11 is interposed between said opening 8 and the face 9 of the patient, when the shell 2 is applied against the face 9.

The respiratory mask 1 also comprises a flexible membrane 13 being inserted at one of its ends 13E, for example by gluing, on the inflatable bead 11 and adapted to be interposed between the latter and the face 9 of the patient on which it can abut. The membrane 13 made in a plastic film with a thickness of a few microns, partially surrounds the bead 11—particularly its external surface opposite the face—and extends, thru its free end 131, toward the inside of the opening 8. The membrane 13 has a bigger flexibility that the inflatable bead 11, thus allowing to be applied, with some adjustment, against the asperities of the face 9.

The mask 1 comprises moreover a multi-perforated internal skirt 14 attached thru one of its two contours 14E, for example by gluing, to the bead 11 and surrounded by the flexible membrane 13. The skirt 14 is preferably in a semi-rigid material—although it could be optionally flexible—and conformed to the face 9 of the patient. It is made in a plastic material, but could also be made of a closed pore foam.

The perforations 15 of the skirt 14 are regularly distributed along the circumference of the latter and arranged opposite the membrane 3 so as to allow for a uniform distribution of the respiratory gas and a perfect application of the membrane 13 against the face 9.

Figure 2:
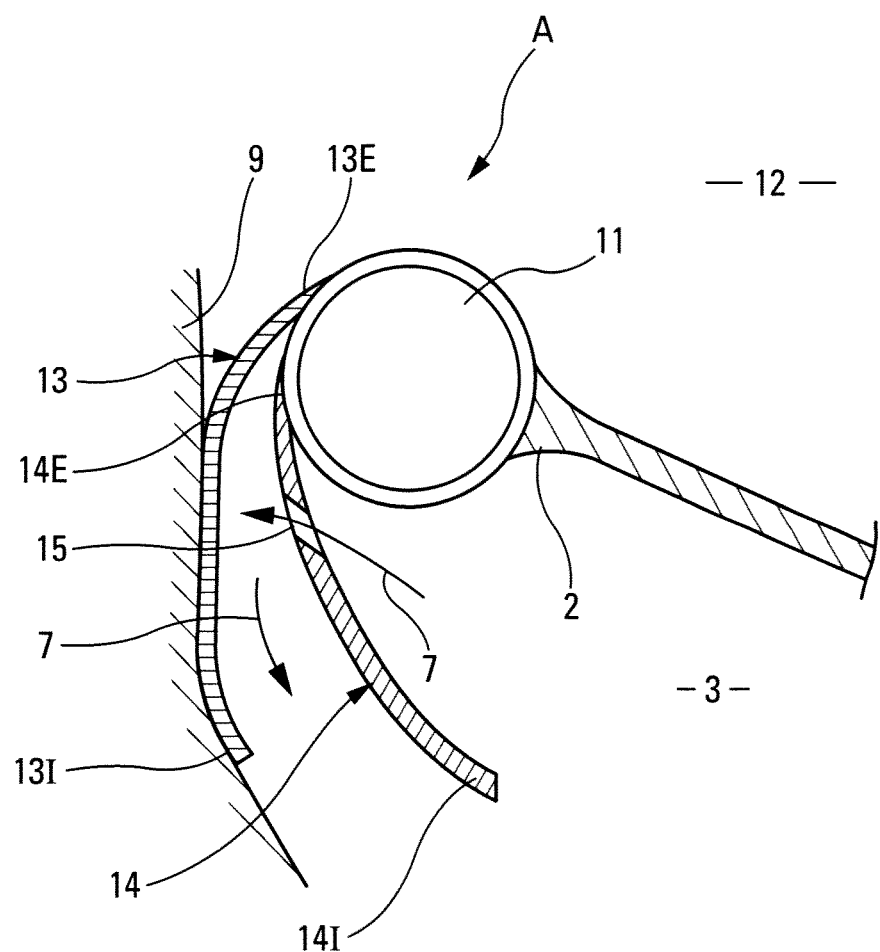
FIG. 2 is an enlarged schematic view of the area A in FIG. 1.

The free contour 141 of the skirt 14 extends inside the internal chamber 3 and participates in the orientation of a part of the air flow 7 toward the perforations 15 of the skirt 14. As shown by the FIGS. 1 and 2, the perforations 15 are present under the form of oblique holes arranged in the skirt 14, so as to orient the respiratory gas toward said membrane 13 while reducing turbulences in the vicinity of the hole inlet.

Thus, when the mask 1 is positioned on the face 9 of the patient, the flexible membrane 13 is interposed between the bead 11 and the face 9 so as to provide a uniform sealing along the opening 8 and seal the internal chamber 3 from the outside 12.

In particular, a part of the respiratory gas 7, entering the shell 2 thru the opening 4 (arrow 7) and passes in the internal chamber 3, crosses the perforations 15 and stretches the membrane 13 so as to apply it against the face 9. Thus, the flexible membrane 13 is easily adapted to the morphology of the face 9 of the patient, by a simple contact on the latter, thus providing a uniform sealing between the face 9 and the mask 1 along the opening 8 without requiring a thorough application of the mask 1 on the face 9. Thanks to the present device, system, and method, the sealing may be obtained by the only membrane 13, although a participation of the bead 11 is also to be envisaged.

Moreover, since the membrane 13 is flexible and elastic and that it presents a free end 131 in the opening 8, the respiratory mask 1 can be automatically adapted to the different morphologies of faces of various dimensions, the flexible membrane 13 being stretched conforming with an adjustment on the latter.

The invention claimed is:

1. A respiratory assistance mask allowing to bring, in the lungs of a patient, respiratory gas from an external source, said mask comprising:
    a hollow body, the internal volume of which defines an internal chamber provided with a respiratory gas inlet adapted to be connected to said source;
    an opening forming the respiratory gas outlet and which is adapted to be connected to a respiratory tract of said patient; and
    a flexible bearing member bordering the contour of said opening and which is adapted to be interposed between the face of said patient and said hollow body,
    wherein it further comprises:
    a flexible membrane inserted on said bearing member and being able to be interposed between said bearing member and the face of said patient; and
    a multi-perforated internal skirt inserted, thru one of the two contours thereof, on said bearing member and surrounded, at least partially, by said flexible membrane, the free contour of said skirt extending in the direction of said internal chamber,
    so that respiratory gas is adapted to cross the perforations of said skirt, from said inlet, so as to stretch said membrane and apply it tightly against patient's face.

2. The mask according to claim 1,
    wherein said perforations are regularly distributed along the circumference of said skirt.

3. The mask according to claim 1,
    wherein said perforations are arranged in said skirt opposite said membrane.

4. The mask according to claim 3,
    wherein each of said perforations is present under the shape of an oblique hole arranged in said skirt so as to orient the respiratory gas toward said membrane.

5. The mask according to claim 1,
wherein the free end of said membrane preferably extends toward the inside of said opening.
6. The mask according to claim 1,
wherein said bearing member is present under the shape of at least one of an inflatable bead or a closed pore foam bead.
7. The mask according to claim 1,
wherein said skirt is shaped to the form of the face.
8. The mask according to claim 1,
wherein said flexible membrane is made in a plastic film of a thickness of a few microns.

* * * * *